US005763642A

United States Patent [19]
Cai

[11] Patent Number: 5,763,642
[45] Date of Patent: Jun. 9, 1998

[54] LOW MONOL POLYOXY (HIGHER) ALKYLENE POLYOLS WITH PRIMARY HYDROXYL CONTENT

[75] Inventor: Gangfeng Cai, West Chester, Pa.

[73] Assignee: ARCO Chemical Technology, L.P., Greenville, Del.

[21] Appl. No.: 878,593

[22] Filed: Jun. 19, 1997

[51] Int. Cl.⁶ .................................................. C07C 69/34
[52] U.S. Cl. .......................... 560/198; 560/199; 560/122; 560/127; 560/89; 560/91; 554/37; 554/121; 554/163; 554/168
[58] Field of Search .................................. 560/198, 199, 560/122, 127, 89, 91; 554/37, 121, 163, 168

[56] References Cited

U.S. PATENT DOCUMENTS 4,440,705  4/1984  Nissen et al. ............................. 264/53
5,470,813  11/1995 Le-Khac ................................... 502/175
5,482,908  1/1996  Le-Khac ................................... 502/156

*Primary Examiner*—Samuel Barts
*Attorney, Agent, or Firm*—Jonathan L. Schuchardt

[57] ABSTRACT

Esterification of an ultra-low unsaturation polyoxy(higher) alkylene polyol with a dicarboxylic acid or reactive derivative thereof to form a poly(half ester) followed by capping the poly(half ester) with a capping agent capable of forming an amide linkage or ester linkage while retaining primary hydroxyl functionality, generates high primary hydroxyl content polyols with substantially retained hydrophile/lipophile balance and low polydispersity. Low color products having primary hydroxyl contents in excess of 80 equivalent percent may be routinely achieved.

20 Claims, No Drawings

LOW MONOL POLYOXY (HIGHER) ALKYLENE POLYOLS WITH PRIMARY HYDROXYL CONTENT

TECHNOLOGICAL FIELD

The present invention pertains to polyoxy (higher) alkylene polyols having low monol content and high primary hydroxyl content. More particularly, the subject invention pertains to polyoxyalkylene polyols prepared by polyoxyalkylation in the presence of ultra-low unsaturation inducing catalysts, which are then chemically modified to provide a high level of terminal primary hydroxyl groups.

DESCRIPTION OF THE RELATED ART

Polyoxyalkylene polyether polyols have a number of uses, including, for example, their use in providing the "soft segments" of polyurethane, polyurethane/urea, and in some cases, polyester polymers. While polyoxyethylene polyols are useful in certain applications, their higher degree of crystallinity, hydrophilicity, and hygroscopicity, restrict their use in many applications where their higher carbon content homologs, predominately polyoxypropylene and polyoxybutylene polyols, have proven satisfactory. The latter polyols, in all but the lowest molecular weight oligomers, are relatively hydrophobic, and are thus compatible with many reactive polymer systems.

However, oxyalkylation of suitably hydric initiator molecules with propylene oxide, butylene oxide, and other higher alkylene oxides, results in polyoxy(higher)alkylene polyols whose terminal hydroxyl groups are largely secondary hydroxyls. Secondary hydroxyl groups are not nearly as reactive as primary hydroxyls. Due to the lower reactivity of the secondary hydroxyl group, the use of homopolymeric polyoxypropylene and polyoxybutylene polyols is rendered difficult if not impossible in such high volume products as high resilience polyurethane slab foam and one shot molded polyurethane foam. In less critical applications such as polyurethane elastomers and prepolymer derived foams, where high secondary hydroxyl polyols may be used in the form of prepolymers to prepare acceptable products, prepolymer processing time is extended, creating an economic penalty at the raw material end rather than the product production end. For these and other reasons, poly(higher) oxyalkylene polyols are often capped with polyoxyethylene groups to provide high primary hydroxyl content.

For example, a 4200 Dalton (Da) molecular weight polyoxypropylene triol prepared by the strong base (KOH) catalyzed polyoxypropylation of glycerine may be "EO-capped" ("ethylene oxide capped") by conducting the last portion of the oxyalkylation with ethylene oxide rather than propylene oxide. Adding enough ethylene oxide to produce a 6000 Da triol (30% EO cap) will introduce polyoxyethylene terminated molecules having substantially higher primary as compared to secondary, hydroxyl content. This procedure has several drawbacks, however. First, because ethylene oxide is polymerized onto the molecules in random fashion, a considerable quantity of cap must be present to produce a high primary hydroxyl content. For example, a 30 weight percent EO cap generally results in only approximately 70–80% primary hydroxyl content. Second, the large amount of polyoxyethylene content considerably alters important properties such as hydrophobicity and hygroscopicity, and may confer often unwanted surfactant properties by establishing or altering hydrophile/lipophile balance.

Low monol polyols are generally prepared by double metal cyanide complex catalyzed polyoxyalkylation. During conventional base catalyzed oxypropylation, a competing rearrangement of propylene oxide into allyl alcohol continually generates an oxyalkylatable unsaturated monol during the course of the reaction. The polyoxyalkylation of this monomeric species produces oligomeric monols of broad molecular weight range, which not only increase polydispersity, but more importantly, decreases the product functionality. For example, polyoxypropylene triols with equivalent weights of 2000 Da may contain 40 mol percent monol, thus lowering the theoretical, or "nominal" functionality from 3.0 to the range of 2.1 to 2.3.

Double metal cyanide complex catalysts (DMC catalysts) such as non-stoichiometric zinc hexacyanocobaltate glyme complexes are able to produce polyoxypropylene polyols with low monol content, as reflected by levels of unsaturation of 0.015 to 0.020 meq/g polyol, as compared to unsaturation of 0.06 meq/g to 0.012 meg/g in moderate to high molecular weight, conventionally base catalyzed polyols. Improvements in DMC catalysts at the ARCO Chemical Company, as reflected by U.S. Pat. Nos. 5,470,813 and 5,482,908, herein incorporated by reference, now allow production of "ultra-low" unsaturation polyols, with unsaturation in the range of 0.003 meq/g or lower, to about 0.010 meq/g. The monol content of polyols produced by these catalysts is exceptionally low, in the worst cases about 2 mol percent, and often virtually unmeasurable. Moreover, the polydispersity of these polyols is exceptionally low. The polyols, in many cases, are essentially monodisperse. However, although DMC catalysts are satisfactory catalysts for polyoxyalkylation of higher alkylene oxides and mixtures of higher alkylene oxides with as much as approximately 80 mol percent ethylene oxide, capping of polyoxy (higher)alkylene polyols solely with ethylene oxide using DMC catalysis to provide high primary hydroxyl content has not heretofore been successful. Ethylene oxide capping employing DMC catalysts leads to considerable quantities of ill-defined coproducts, believed to be homopolyoxyethylene glycols.

Ethylene oxide capping of DMC catalyzed polyoxy (higher)alkylene polyols may be accomplished by purifying the polyol to remove the DMC catalyst, followed by addition of another oxyalkylation catalyst. Another technique is to denature the DMC catalyst by adding an excess of strong alkali metal base, the excess serving as the polyoxyethylation catalyst. However, these methods require adsorption, neutralization, and/or filtration of the generally rather viscous polyol product to remove basic catalyst residues, increasing cost of the product. Moreover, the polyoxyethylene capping ("EO capping") suffers from the same drawbacks as the EO capping of conventional, base-catalyzed polyols: the capping is both inefficient and further alters the physical characteristics of the polyol. It is especially difficult to prepare high primary hydroxyl polyoxy(higher)alkylene polyols with low molecular weights without grossly altering polyol properties.

It would be desirable to provide a process for the preparation of low monol polyoxy(higher)alkylene polyols with high primary hydroxyl content without significantly altering other polyol properties. It would be further desirable to prepare low molecular weight polyoxy(higher)alkylene polyols with high primary hydroxyl contents, and to prepare such high primary hydroxyl polyols without resorting to the use of a polyoxyethylene cap.

SUMMARY OF THE INVENTION

It has now been discovered that low monol polyoxy (higher)alkylene polyols with high primary hydroxyl content may be prepared by polyesterifying a polyoxy(higher) alkylene polyol with an excess of a difunctional carboxylic acid or reactive derivative thereof, followed by esterification of the resultant poly(half ester) with a diprimary glycol or polyol. The products have substantially the same hydrophile/lipophile balance as the polyoxy(higher)alkylene polyprecursor, have low color, and acceptable polydispersity.

DESCRIPTION OF THE PREFERRED EMBODIMENTS

The high primary hydroxyl content polyols of the subject invention are prepared by reacting a polyoxy(higher) alkylene polyol with a dicarboxylic acid or reactive derivative thereof to form a half ester functional polyol (poly(half ester)), following which the remaining carboxylic acid groups of the half ester functionality are capped with a primary hydroxyl group-containing capping agent with retention of primary hydroxyl functionality. Preferably, the dicarboxylic acid or its derivative is a saturated or aromatic-group containing dicarboxylic acid free of ethylenic unsaturation.

Although a spectrum of reaction products are obtained through the subject process, the majority of such products consist of moieties having the formula:

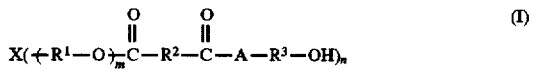
$$X(\!+\!R^1\!-\!O)_{\overline{m}}C\!-\!R^2\!-\!C\!-\!A\!-\!R^3\!-\!OH)_n \qquad (I)$$

wherein X is the residue of an initiator molecule having n oxyalkylatable hydrogen atoms; each $R^1$—O represents an oxyalkylene moiety which may be the same or different, wherein at least 20 mol percent of $R^1$ are $C_{3-20}$ hydrocarbon radicals; wherein m is such that

$$X(\!+\!R^1\!-\!O)_{\overline{m}}H)_n \qquad (II)$$

has an equivalent weight in excess of about 500 Da, and wherein (II) has a primary hydroxyl content of less than about 50 equivalent percent; wherein $R^2$ is a $C_{2-30}$ hydrocarbon radical free of ethylenic unsaturation, optionally interspersed with hetero atoms, wherein A is —NH— or —O—; wherein $R^3$ is a $C_{2-20}$ hydrocarbon optionally interspersed with heteroatoms, the residue of an oligomeric polyoxyalkylene moiety having a molecular weight of about 300 Da or less, and originally bearing at least one primary hydroxyl group and a second reactive functionality selected from the group consisting of a primary amino group and a second primary hydroxyl group; wherein the average unsaturation of (II) is less than about 0.020 mq/g, and wherein the number of primary hydroxyl groups in the —$R^3$—OH moiety on average is such that (I) has a measured primary hydroxyl content of greater than about 70 equivalent percent.

The subject process is useful in preparing not only mixtures containing the moiety (I) above, where $R^2$ is a hydrocarbon free of ethylenic unsaturation, but may be used to form unsaturated analogs as well. The subject process for the preparation of a high primary hydroxyl content ultra-low unsaturation polyoxy(higher)alkylene polyol, involves selecting an ultra-low unsaturation polyoxy(higher)alkylene polyol with a functionality of two or more and an equivalent weight of about 500 or more; esterifying the ultra-low unsaturation polyoxy-(higher)alkylene polyol with a dicarboxylic acid or reactive derivative thereof to form a poly (half ester); and reacting the remaining carboxyl functionalities of said poly(half ester) with a capping agent which generates, upon said reacting, an ester linkage or amide linkage, and which retains a primary hydroxyl group. The product preferably has a number average molecular weight which is less than twice the molecular weight of the base polyoxy(higher)alkylene polyol.

The low monol polyoxy(higher)alkylene polyols are prepared by addition polymerization of one or more higher alkylene oxides onto an initiator molecule of appropriate functionality. By the term "higher alkylene oxide" is meant an oxirane other than ethylene oxide. Examples of higher alkylene oxides include propylene oxide, 1,2-butylene oxide, 2,3-butylene oxide, cyclohexene oxide, and the like. The higher alkylene oxides have carbon contents of $C_3$ to $C_{20}$, in general. Alkylene oxides which are not oxiranes, e.g. oxetane, and tetrahydrofuran, are not "higher alkylene oxides" as that term is used herein. However, under appropriate circumstances, these monomers may be used in conjunction with a higher alkylene oxide. Furthermore, ethylene oxide may be used in conjunction with the higher alkylene oxide for all or part of the oxyalkylation, in amounts up to 80 mol percent of the oxide feed, preferably in amounts of up to 50 mol percent, more preferably less than 25 mol percent.

By the term polyoxy(higher)alkylene polyol is meant a polyether polyol prepared by polyoxyalkylation of one or more higher alkylene oxides, optionally in conjunction with oxetane, tetrahydrofuran, other copolymerizable monomers as disclosed in U.S. Pat. Nos. 3,404,109; 3,538,043; and 5,145,883, herein incorporated by reference, or ethylene oxide. The polyoxy(higher)alkylene polyol should have a secondary hydroxyl content of greater than 50 mol percent, and an equivalent weight of 500 Da to about 10,000 Da or higher, preferably 1000 Da to 4000 Da, and more preferably 1000 Da to 6000 Da. Molecular weights and equivalent weights expressed herein in Da (Daltons) are number average molecular weights and equivalent weights unless indicated otherwise.

The initiator molecules are suitably hydric initiator molecules. By "suitably hydric" is meant an initiator molecule with a number of oxyalkylatable hydrogens so as to provide the desired nominal functionality. Nominal functionalities of from two to eight or higher are preferred. Preferred initiator molecules include difunctional initiators such as ethylene glycol, diethylene glycol, propylene glycol, dipropylene glycol, 1,4-butanediol, 1,6-hexanediol, neopentylglycol, 1,4-cyclohexanediol, 1,4-cyclohexanedimethanol, and 1,4-hydroquinone; trifunctional initiator molecules such as glycerine, trimethylolpropane, trimethylolethane, diethanolamine, and triethanolamine; tetrafunctional initiators such as pentaerythritol, the various N,N,N',N'-tetrakis [2-hydroxyalkyl]alkylene diamines, N,N,N',N'-tetrakis[2-hydroxyalkyl]-4,4'-methylene-dianiline, and saccharides having four hydroxyl groups; hexahydric initiators such as sorbitol and other saccharides having six hydroxyl groups; and octahydric initiators such as sucrose. Mixtures of various initiators may be used as well.

The oxyalkylation takes place under oxyalkylation conditions suitable for the chosen "low monol" oxyalkylation catalyst. These conditions are by now well known to those skilled in the art. When the oxyalkylation catalyst is a DMC catalyst, the higher alkylene oxide is generally added in minor portion to an initiator/catalyst mixture, and agitated at the desired oxyalkylation temperature until a reduction in concentration of alkylene oxide indicates that the "induction period" associated with DMC catalysts is over and the catalyst has been activated. For example, when propylene oxide or other volatile alkylene oxide is used, the reactor pressure may be monitored. Further details of oxyalkylation employing DMC catalysts may be obtained from U.S. Pat. Nos. 5,470,813 and 5,482,908, which have been incorporated by reference. Oxyalkylation is continued with a single alkylene oxide or mixture of alkylene oxides or other copolymerizable monomers until the desired molecular weight is obtained. The polyol is then purified free of catalysts by conventional techniques, where necessary.

Following preparation of the polyoxy(higher)alkylene polyol, the polyol is reacted with the dicarboxylic acid or reactive derivative to form a poly(half ester). By the term "dicarboxylic acid or reactive derivative" is meant an organic dicarboxylic acid or derivative which is capable of forming two ester linkages by reaction with hydroxyl groups. Examples of dicarboxylic acid "reactive derivatives" include dicarboxylic acid anhydrides, dicarboxylic acid monohalides, dicarboxylic acid dihalides, and the like. Examples of suitable dicarboxylic acids and reactive derivatives include adipic acid, adipic acid anhydride, adipoyl chloride, terephthalic acid, terephthaloyl chloride, butanedioic acid, maleic acid, maleic anhydride, succinic anhydride, succinyl chloride, and the like. This list is exemplary only, and not limiting. The dicarboxylic acid organic residues are preferably $C_{2-20}$ hydrocarbons, which may be aliphatic, cycloaliphatic, aromatic, arylaliphatic, alkaryl, and the like. The hydrocarbon residues may be substituted by non-reactive groups such as cyano, halo, trialkylsiloxy, and the like, and may contain interspersed heteroatoms, particularly O,S, and N. Most preferably, the hydrocarbon residues contain no ethylenic or acetylenic (ethylynic) unsaturation.

In general, the dicarboxylic acid or reactive derivative is used in stoichiometric excess to avoid chain-extending polyesterification to higher molecular weight products. Amounts of dicarboxylic acid or reactive derivative is preferably from 1.1 to about 2.0 moles per mol of hydroxyl groups. In the case of dicarboxylic and dihalides, the product initially formed will not contain half ester groups, but will have the polyoxyalkylene base polyol termini linked to the hydrocarbon residue of the reactive derivative by an ester linkage, leaving a free carboxyl halide group. Such products are still poly(half esters) as that term is used herein, as their further reaction with glycol will create the desired bis(ester) product.

For polyoxy-(higher)alkylene polyols with functionalities of three or higher, particularly four or higher, it is preferable that a reactive derivative which reacts in a two-step fashion to rapidly form an initial half-ester linkage under mild conditions be used. Examples of the latter are anhydrides such as maleic anhydride, succinic anhydride, and dicarboxylic acid monohalides. In the case of cyclic dicarboxylic acid anhydrides, the anhydride linkage is cleaved by reaction with hydroxyl groups to form a half ester under relatively mild conditions. The remaining free carboxylic acid group is less reactive. In the case of dicarboxylic acid monohalides, the carboxy halide group reacts rapidly to form an ester linkage, leaving, again, a less reactive carboxylic acid group. In this manner, the amount of oligomeric polyester products and crosslinking is minimized. This reaction sequence is operable with polyoxy(higher)alkylene diols, as well, and allows use of dicarboxylic acid reactive derivatives in amounts closer to stoichiometry based on hydroxyl content.

The esterification may take place neat, but is preferably conducted in a non-reactive organic solvent or azeotropic agent. Preferred solvents are toluene and xylene, as a water/toluene or water/xylene azeotrope may be removed by distillation, collected, and the amount of water which separates from the distillate used to monitor the course of the esterification. Reaction conditions are standard esterification/transesterification conditions well known to those skilled in the art of organic synthesis. The esterification to form the half ester generally takes place at temperatures higher than 100° C, for example 150° C. to 250° C., preferably 170° C. to 220° C., and most preferably about 190° C. to 200° C. Esterification/transesterification catalysts, i.e. metal naphthenates, p-toluenesulfonic acid, and the like may be added as desired. When strong acid catalysts are used, some polyether cleavage may occur, which may broaden the product molecular weight distribution and lower molecular weight accordingly. When anhydrides are used, organic bases such as pyridine may be used as catalysts. The resulting poly(half ester) may be isolated by standard methods, or may be used as such for the attachment of the primary hydroxyl cap. Unreacted diacid may be removed from the product by filtration and/or distillation, or may be retained in the product if low molecular weight bis(glycol) esters can be tolerated.

To prepare the high primary hydroxyl product, a capping agent which is reactive with the remaining carboxylic acid functionality of the poly(half ester) and which carries a primary hydroxyl group is added. Most preferably, this capping agent is a simple alkylene diprimary diol such as ethylene glycol, 1,4-butanediol, 1,6-hexane diol, neopentyl glycol, 2-methylpropane diol, or the like, or a low molecular weight oligomer such as diethylene glycol, triethylene glycol, and the like. Alternatively, the molecule may have one reactive functionality more reactive with carboxylic acid moieties than a primary hydroxyl group, such as an amino group. Examples of such molecules are 3-aminopropanol, monoethanolamine, and the like. In either case, the capping is conducted under esterification or amidation conditions depending upon the particular carboxylic acid reactive functionality chosen. Reaction temperature is selected accordingly. When diprimary diols are used, the capping conditions are generally the same as those used to form the polyol half ester. Progress of the reaction may be monitored by analysis for acid number, or by measuring the amount of water produced by the condensation reaction. For special purposes, a molecule with more than two post-reaction primary hydroxyl groups such as triethanolamine may be used. The capping agent is used in stoichiometric excess, for example in an amount of 1.1 to 1.5 moles of capping agent per mol of hydroxyl groups in the original polyoxy-(higher) alkylene polyol. Reaction is preferably continued until an acid number of 1.5 mg KOH/g polyol or less is achieved.

The resulting high primary hydroxyl content, polyoxy (higher)alkylene polyols may be used for all purposes where high primary hydroxyl content is achieved by extensive polyoxyethylene capping. However, unlike polyoxy(higher) alkylene polyols such as polyoxyethylene capped polyoxypropylene glycols, the high primary hydroxyl content polyols of the subject invention have a hydrophile/lipophile balance similar to the base polyoxypropylene glycol. Moreover, the lack of extensive, hydrophilic polyoxyethylene cap renders polymers prepared from the subject polyols much less subject to water adsorption.

Having generally described this invention, a further understanding can be obtained by reference to certain specific examples which are provided herein for purposes of illustration only and are not intended to be limiting unless otherwise specified. In the Examples which follow, acid numbers are reported in mg KOH/g polyol. Viscosities are measured by a Brookfield viscometer Model LVF, in 4 oz. French bottles containing 100 g polyol at 20° C. Primary hydroxyl contents are measured based on $^1$H and $^{13}$C NMR by standard techniques.

EXAMPLE 1

A high primary hydroxyl polyoxypropylene diol was prepared using an ultra-low unsaturation 4000 Da homopolyoxypropylene diol as the base polyoxy(higher) alkylene polyol, adipic acid as the dicarboxylic acid, and 1,4-butanediol as the diprimary glycol capping agent. To 1183 g of ultra-low unsaturation 4000 Da polyoxypropylene diol was added 250 g adipic acid and 80 grams toluene. The temperature was raised to 190° C. ±3° C and held for a period of 6 hours. From time to time, additional toluene was added when necessary to remove adipic acid from the flask and condenser walls. A total of 9.6 g water was collected as an azeotrope with toluene. The intermediate polyoxypropylene bis(half ester) was filtered through a coarse paint filter.

To the filtered product was added 207 g 1,4-butanediol. The mixture was heated to 190° C. to 200° C. until the acid number dropped to 1.2 meq KOH/g. Product acid number, polydispersity, viscosity, and other properties are listed in Table 1. The values in the table are those of the product as isolated

EXAMPLE 2

To 6698 g of ultra-low unsaturation 4000 Da molecular weight polyoxypropylene diol was added 500 g adipic acid and 350 g xylene. The mixture was stirred and heated to a temperature of 190° C. to 200° C., water being collected as an overhead with xylene. After collection of the theoretical amount of water, the product bis(half ester) in the amount of 6976 grams was transferred to a clean flask and a two fold excess (627.4 g) 1,4-butanediol added. The mixture was heated to 190° C. until the acid number reached 2.60 at which time the excess 1,4-butanediol was removed by distillation in vacuo. Product properties are listed in Table 1.

EXAMPLE 3

An ultra-low unsaturation polyoxypropylene diol of 2000 Da molecular weight, sold by the ARCO Chemical Company under the tradename ACCLAIMS™ polyol, in the amount of 8373 grams, was added to a reaction kettle and 1254.2 g adipic acid added. To the mixture was added 200 g xylene to aid in water removal, and 2.4 g p-toluenesulfonic acid as an esterification catalyst. After the mixture reached the desired reaction temperature of 195° C, an additional 113 g xylene was added. Additional xylene was added as desired during the course of the reaction, which was terminated when the acid number reached 41.4 mg KOH/g. The bis (half ester) was drained into gallon bottles for later capping.

EXAMPLE 4

A two liter reactor was charged with 1500 g of a bis(half ester) prepared from a 2000 Da ultra-low unsaturation homopolyoxypropylene diol and adipic acid in a manner similar to that of Example 3, 100 g methylpropanediol, and 50 g xylene. The reactor was heated to 195° C. After 90 minutes, the acid number had dropped to 25.5. Two hours later, 0.4 g p-toluenesulfonic acid was added as an esterification catalyst. When the acid number dropped to 6.5, an additional 25 g methylpropanediol was added, with a further addition of 100 g methylpropanediol and 50 g xylene when the acid number reached 2.23. The reaction was terminated when the acid number reached 1.04, and excess methylpropanediol removed in vacuo. The high primary hydroxyl polyol was bottled. Properties are given in Table 1.

EXAMPLES 5-10

In a similar fashion, a variety of high primary hydroxyl content polyols were prepared from 2000 Da and 4000 Da ultra-low unsaturation diols as the polyoxy(higher)alkylene polyol, adipic acid as the dicarboxylic acid, and 1,4-butanediol(BDO), neopentylglycol (NPG), or methylpropanediol (MPD) as the capping agent. Physical and chemical characteristics are presented in Table 1.

TABLE 1

| Example | Polyol  | Capping Agent | Hydroxyl No. mgKOH/gm | Primary OH (%) | Acid No. mgKOH/gm | Mn   | Mw/Mn | Viscosity (cps) |
|---------|---------|---------------|-----------------------|----------------|-------------------|------|-------|-----------------|
| Control | 2000 Da | none          | 56.1                  | 15%            | —                 | 2000 | 1.03  | 465             |
| 1       | 4000 Da | BDO           | 34.6                  | 83.2           | 1.1               |      |       | 2025            |
| 2       | 4000 Da | BDO           | 36.7                  | 85.1           | 2.9               |      |       | 2350            |
| 4       | 2000 Da | MPD           | 32.2                  | 82.7           | 0.85              | 2975 | 1.93  | 3880            |
| 5       | 2000 Da | NPG           | 37.5                  | 80.7           | 1.35              | 2975 | 1.84  | 3495            |
| 6       | 2000 Da | BDO           | 39.6                  | 75.3           | 0.56              | 2541 | 1.68  | 1875            |
| 7       | 4000 Da | MPD           | 43.3                  | 87.5           | 0.52              | 2064 | 1.65  | 1475            |
| 8       | 4000 Da | NPG           | 31.2                  | 84.7           | 0.95              | 2595 | 1.90  | 2475            |
| 9       | 4000 Da | BDO           | 35.5                  | 76.5           | 0.56              | 3116 | 1.86  | 1875            |
| 10      | 2000 Da | BDO           | 51.2                  | 70.9           | 0.79              | 2881 | 1.72  | 2000            |

As the Examples reported indicate, the high primary hydroxyl polyols have low acid numbers and very high primary hydroxyl content. At the same time, the hydrophile/lipophile balance of the base polyol is substantially maintained. The hydroxyl numbers appear to indicate that some chain extension has occurred. However, the amount is believed small, as reflected by the relatively low polydispersities of the product. The low molecular weights probably indicate that initial half-esterification was not complete in some cases, allowing excess capping agent to react with remaining dicarboxylic acid. The process has not been optimized. The characteristics of an ultra-low unsaturation, 2000 Da molecular weight diol are included for comparison purposes. Note that a conventional, base-catalyzed diol would have a significantly higher viscosity than the ultra-low unsaturation diol.

What is claimed is:

1. A high primary hydroxyl content polyoxy(higher) alkylene polyol, comprising moieties having the formula:

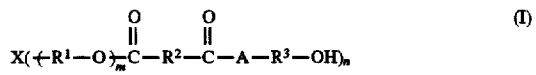

wherein X is the residue of an initiator molecule having n oxyalkylatable hydrogen atoms; each $R^1$—O represents an oxyalkylene moiety which may be the same or different, wherein at least 20 mol percent of $R^1$ are $C_{3-20}$ hydrocarbon radicals; wherein m is such that

has an equivalent weight in excess of about 500 Da, and wherein (II) has a primary hydroxyl content of less than about 50 equivalent percent; wherein $R^2$ is a $C_{2-30}$ hydrocarbon radical free of ethylenic unsaturation, optionally interspersed with hetero atoms, wherein A is —NH— or —O—; wherein $R^3$ is a $C_{2-20}$ hydrocarbon optionally interspersed with heteroatoms or the residue of an oligomeric polyoxyalkylene moiety having a molecular weight of about 300 Da or less, each originally bearing at least one primary hydroxyl group and a second reactive functionality selected from the group consisting of a primary amino group and a second primary hydroxyl group; wherein the average unsaturation of (II) is less than about 0.020 mq/g, and wherein the number of primary hydroxyl groups in the —$R^3$—OH moiety on average is such that (I) has a measured primary hydroxyl content of greater than about 70 equivalent percent.

2. The product of claim 1 wherein said at least 20 mol percent $R^1$ are $C_3$ and/or $C_4$ hydrocarbon radical(s); each $R^2$ individually is a $C_2$-$C_4$ saturated aliphatic hydrocarbon radical, $C_5$-$C_6$ cycloaliphatic hydrocarbon radical, or $C_6$-$C_{10}$ aryl radical.

3. The product of claim 1 wherein m is such that (II) has an equivalent weight of from about 1000 Da to about 6000 Da.

4. The product of claim 1 wherein (II) has an unsaturation of less than about 0.010 meq/g.

5. The product of claim 1 wherein the polydispersity of said product is less than about 2.5.

6. The product of claim 1 wherein $R^2$ is

7. The product of claim 1 wherein $R^3$ is selected from the group consisting of $C_2$-$C_6$ alkylene, $C_2$-$C_6$ alkylene substituted by one or more $C_1$-$C_4$ alkyl groups, and mixtures thereof.

8. The product of claim 1 wherein —$R^3$—OH is the primary hydroxyl-containing residue of an aliphatic glycol selected from the group consisting ethylene glycol, 1,4-butanediol, 1,6-hexanediol, neopentyl glycol, and 2-methylpropanediol.

9. The product of claim 1 wherein m is such that (II) has an equivalent weight of about 1000 Da to about 4000 Da, n is from 2 to 3, in excess of 50 mol percent of $R^1$—O are oxypropylene groups; $R^2$ -(CH$_2$)$_4$-, A is —O—, and $R^3$ is selected from the group consisting of

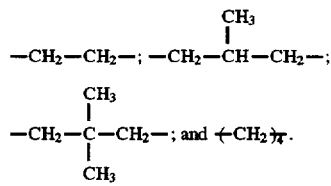

10. A process for the preparation of a high primary hydroxyl content, low unsaturation polyoxy(higher)alkylene polyol, comprising:

a) selecting a low unsaturation polyoxy(higher)alkylene base polyol with a functionality of two or more, an unsaturation less than about 0.020 meq/g, and an equivalent weight of about 500 Da or more;

b) esterifying said ultra-low unsaturation polyoxy(higher) alkylene base polyol with a dicarboxylic acid or reactive derivative thereof to form a poly(half ester);

c) reacting the remaining carboxyl functionality of said poly(half ester) with a capping agent which generates, upon said reacting, an ester linkage or amide linkage, and which retains a primary hydroxyl group following said reacting, wherein said high primary hydroxyl content ultra-low unsaturation polyoxy(higher) alkylene polyol has a number average molecular weight which is less than twice the number average molecular weight of said polyoxy(higher)alkylene base polyol, and a primary hydroxyl content in excess of about 70 equivalent percent.

11. The process of claim 10 wherein said dicarboxylic acid or reactive derivative thereof is a saturated or unsaturated $C_2$-$C_{30}$ dicarboxylic acid or anhydride thereof.

12. The process of claim 11 wherein said dicarboxylic acid or derivative thereof is adipic acid, adipic anhydride, or mixtures thereof.

13. The process of claim 11 wherein said dicarboxylic acid anhydride is a cyclic anhydride.

14. The process of claim 10 wherein said dicarboxylic acid or reactive derivative thereof is used in an amount of 1.1 to 2.0 mol per mol of hydroxyl groups of said polyoxy (higher)alkylene base polyol.

15. The process of claim 10 wherein said capping agent comprises a primary alkanolamine or a diprimary hydroxyl group-containing glycol.

16. The process of claim 10 wherein said capping agent comprises a $C_{2-20}$ aliphatic glycol.

17. The process of claim 10 wherein said capping agent is used in an amount of from about 1.1 to about 1.5 mol per mol of hydroxyl groups in said polyoxy(higher)alkylene base polyol.

18. The process of claim 1 wherein a stoichiometric excess of dicarboxylic acid or reactive derivative thereof is used, and following preparation of said poly(half ester), said poly(half ester) is freed of excess dicarboxylic acid or reactive derivative thereof.

19. The process of claim 10 wherein said capping agent is used in stoichiometric excess, and following preparation of said high primary hydroxyl content low unsaturation polyoxy(higher)alkylene polyol, excess capping agent is removed via distillation and/or stripping.

20. A high primary hydroxyl content polyoxy(higher) alkylene polyol prepared by the process of claim 10.

* * * * *